(12) United States Patent
Brehm et al.

(10) Patent No.: US 11,638,823 B2
(45) Date of Patent: May 2, 2023

(54) HEADPIECES AND IMPLANTABLE COCHLEAR STIMULATION SYSTEMS INCLUDING THE SAME

(71) Applicant: ADVANCED BIONICS AG, Staefa (CH)

(72) Inventors: Andreas Benedikt Brehm, Houston, TX (US); Markus Trautner, Marina Del Rey, CA (US); James George Elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 39 days.

(21) Appl. No.: 17/335,161

(22) Filed: Jun. 1, 2021

(65) Prior Publication Data

US 2021/0339021 A1 Nov. 4, 2021

Related U.S. Application Data

(63) Continuation of application No. 16/966,885, filed as application No. PCT/US2018/018451 on Feb. 15, 2018, now abandoned.

(51) Int. Cl.
*A61N 1/372* (2006.01)
*A61N 1/36* (2006.01)

(52) U.S. Cl.
CPC ...... *A61N 1/36038* (2017.08); *A61N 1/37211* (2013.01)

(58) Field of Classification Search
None
See application file for complete search history.

(56) References Cited

U.S. PATENT DOCUMENTS

| | | |
|---|---|---|
| 4,214,366 A | 7/1980 | Laban |
| 4,352,960 A | 10/1982 | Dormer et al. |
| 4,595,390 A | 6/1986 | Hakim et al. |
| 4,606,329 A | 8/1986 | Hough |
| 4,612,915 A | 9/1986 | Hough et al. |
| 4,618,949 A * | 10/1986 | Lister ............... G01V 1/16 367/185 |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |

(Continued)

FOREIGN PATENT DOCUMENTS

| | | |
|---|---|---|
| CN | 212542072 U | 2/2021 |
| DE | 202006017662 U1 | 9/2007 |

(Continued)

OTHER PUBLICATIONS

U.S. Appl. No. 16/499,311, filed Sep. 29, 2019, 20210106815 A1.

(Continued)

*Primary Examiner* — Erica S Lee
(74) *Attorney, Agent, or Firm* — Henricks Slavin LLP

(57) ABSTRACT

A cochlear implant headpiece, for use with a cochlear implant, including a housing, a diametrically magnetized headpiece magnet, defining an axis and a N-S direction, within the housing and rotatable about the axis, whereby the N-S direction of the headpiece magnet self-aligns with the gravitational direction when the axis is perpendicular to the gravitational direction, and a headpiece antenna associated with the housing.

20 Claims, 11 Drawing Sheets

(56) References Cited

U.S. PATENT DOCUMENTS

| | | | |
|---|---|---|---|
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,266,208 B2 | 9/2007 | Charvin et al. |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,027,735 B1 | 9/2011 | Tziviskos et al. |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B1 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 10,532,209 B2 | 1/2020 | Lee et al. |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 | 11/2020 | Lee et al. |
| 11,097,095 B2 | 8/2021 | Smith et al. |
| 11,287,495 B2 | 3/2022 | Smith et al. |
| 11,364,384 B2 | 6/2022 | Smith et al. |
| 11,471,679 B2 | 10/2022 | Smith et al. |
| 11,476,025 B2 | 10/2022 | Lee et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0015155 A1 | 1/2006 | Charvin et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0192968 A1 | 8/2008 | Ho et al. |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0036458 A1* | 2/2010 | Duftner ............ A61N 1/37229 607/57 |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1* | 10/2011 | Zimmerling ....... A61N 1/36038 607/60 |
| 2012/0296155 A1 | 11/2012 | Ball |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0336447 A1 | 11/2014 | Bjorn et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0094521 A1 | 4/2015 | Neuman et al. |
| 2015/0100109 A1 | 4/2015 | Feldman et al. |
| 2015/0112407 A1 | 4/2015 | Hartley et al. |
| 2015/0265842 A1 | 9/2015 | Ridler |
| 2015/0320523 A1 | 11/2015 | Way et al. |
| 2015/0367126 A1 | 12/2015 | Smyth |
| 2015/0374989 A1 | 12/2015 | Hazard et al. |
| 2015/0382114 A1 | 12/2015 | Andersson et al. |
| 2016/0008596 A1 | 1/2016 | Gibson et al. |
| 2016/0023006 A1 | 1/2016 | Ridler et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1* | 7/2016 | Heerlein ............ A61N 1/37229 |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2017/0347208 A1 | 11/2017 | Jurkiewicz |
| 2018/0028818 A1 | 2/2018 | Anderson et al. |
| 2018/0056084 A1 | 3/2018 | Alam |
| 2018/0110985 A1 | 4/2018 | Walter |
| 2018/0110986 A1 | 4/2018 | Lee |
| 2018/0133486 A1 | 5/2018 | Smith |
| 2018/0146308 A1 | 5/2018 | Leigh et al. |
| 2018/0160241 A1 | 6/2018 | Gustafsson et al. |
| 2018/0160242 A1 | 6/2018 | Sriskandarajah |
| 2018/0185634 A1 | 7/2018 | Smyth |
| 2018/0249262 A1 | 8/2018 | Santek |
| 2018/0270591 A1 | 9/2018 | Kennes |
| 2018/0296826 A1 | 10/2018 | Lee et al. |
| 2018/0303602 A1 | 10/2018 | Leigh |
| 2018/0304078 A1 | 10/2018 | Crawford et al. |

(56) References Cited

U.S. PATENT DOCUMENTS

| | | | |
|---|---|---|---|
| 2018/0369586 A1 | 12/2018 | Lee et al. | |
| 2019/0015662 A1 | 1/2019 | Raje et al. | |
| 2019/0046797 A1 | 2/2019 | Calixto et al. | |
| 2019/0053908 A1 | 2/2019 | Cook et al. | |
| 2019/0076649 A1* | 3/2019 | Lee | A61N 1/086 |
| 2019/0255316 A1 | 8/2019 | Lee et al. | |
| 2019/0298417 A1 | 10/2019 | Barrett et al. | |
| 2020/0114151 A1 | 4/2020 | Smith et al. | |
| 2020/0230422 A1 | 7/2020 | Gibson et al. | |
| 2020/0238088 A1 | 7/2020 | Smith et al. | |
| 2020/0330777 A1 | 10/2020 | Smith et al. | |
| 2020/0391023 A1 | 12/2020 | Lee et al. | |
| 2021/0046311 A1 | 2/2021 | Brehm et al. | |
| 2021/0106815 A1 | 4/2021 | Smith et al. | |
| 2021/0156934 A1 | 5/2021 | Smith et al. | |
| 2021/0299456 A1 | 9/2021 | Smith et al. | |
| 2021/0316136 A1 | 10/2021 | Smith et al. | |
| 2022/0273948 A1 | 9/2022 | Calixto et al. | |
| 2022/0280793 A1 | 9/2022 | Smith et al. | |

FOREIGN PATENT DOCUMENTS

| | | |
|---|---|---|
| EP | 0241307 A2 | 10/1987 |
| EP | 2117489 B1 | 5/2010 |
| EP | 2853287 A1 | 4/2015 |
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004004416 A1 | 1/2004 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2012010195 A1 | 1/2012 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018200347 A1 | 11/2018 |
| WO | WO2018217187 A1 | 11/2018 |
| WO | WO2019027745 A1 | 2/2019 |
| WO | WO2019083540 A1 | 5/2019 |
| WO | WO2019160555 A1 | 8/2019 |
| WO | WO2020092185 A1 | 5/2020 |
| WO | WO2021201845 A1 | 10/2021 |

OTHER PUBLICATIONS

U.S. Appl. No. 16/603,868, filed Oct. 9, 2019, 20200114151 A1.
U.S. Appl. No. 16/754,126, filed Apr. 6, 2020, 20200330777 A1.
U.S. Appl. No. 16/966,885, filed Aug. 1, 2020, 20210046311 A1.
PCT International Search and Written Opinion dated Feb. 27, 2019 for PCT App. Ser. No. PCT/US2018/018451.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
U.S. Appl. No. 17/073,322, filed Oct. 17, 2020.
U.S. Appl. No. 17/008,291, filed Aug. 31, 2020, 20200391023 A1.
U.S. Appl. No. 16/610,502, filed Nov. 2, 2019, 20210156934 A1.
U.S. Appl. No. 17/355,225, filed Jun. 23, 2021.
U.S. Appl. No. 17/346,343, filed Jun. 14, 2021.
U.S. Appl. No. 15/568,469, filed Oct. 21, 2017, 20180110985 A1.
U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aug. 31, 2020, U.S. Pat. No. 11,476,025.
U.S. Appl. No. 16/610,502, filed Nov. 2, 2019, U.S. Pat. No. 11,287,495.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 17/680,217, filed Feb. 24, 2022, 20220273948 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, 20210316136 A1.
U.S. Appl. No. 16/603,868, filed Oct. 9, 2019, U.S. Pat. No. 11,364,384.
U.S. Appl. No. 17/750,352, filed May 22, 2022, 20220280793 A1.
U.S. Appl. No. 16/754,126, filed Apr. 6, 2020, U.S. Pat. No. 11,471,679.
U.S. Appl. No. 17/346,343, filed Jun. 14, 2021, 20210299456 A1.
U.S. Appl. No. 17/499,813, filed Oct. 12, 2021.

* cited by examiner

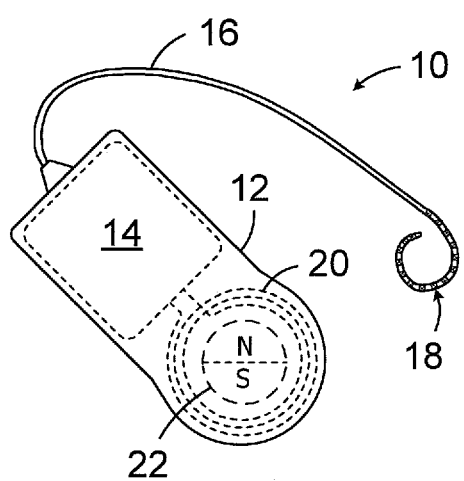
FIG. 1
Prior Art
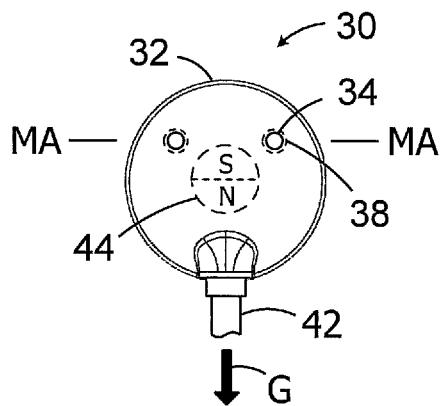
FIG. 2
Prior Art
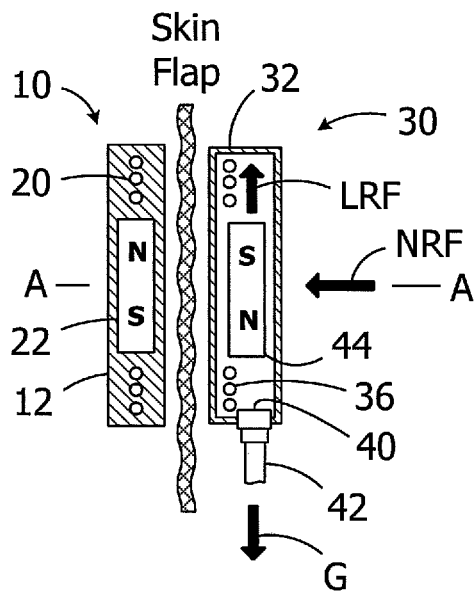
FIG. 3
Prior Art
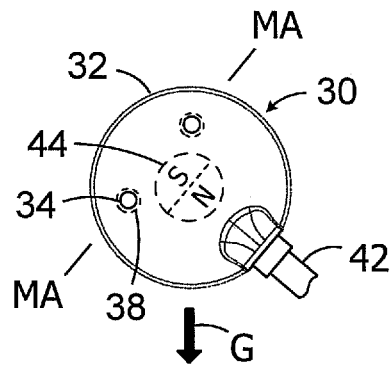
FIG. 4
Prior Art
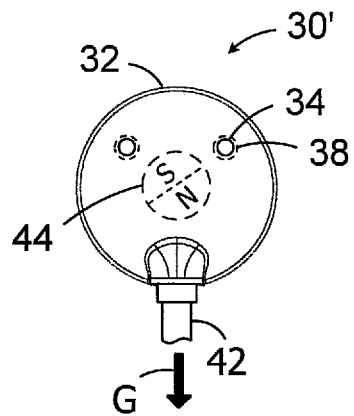
FIG. 5 - Prior Art

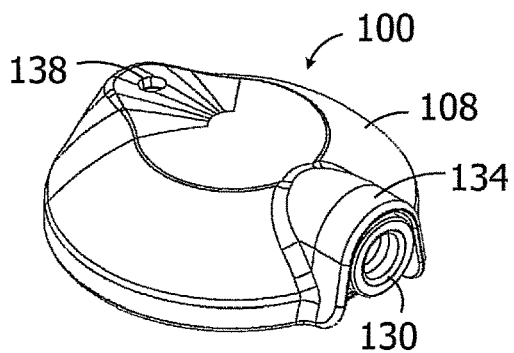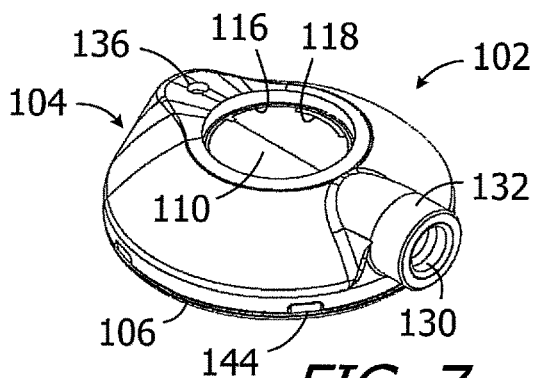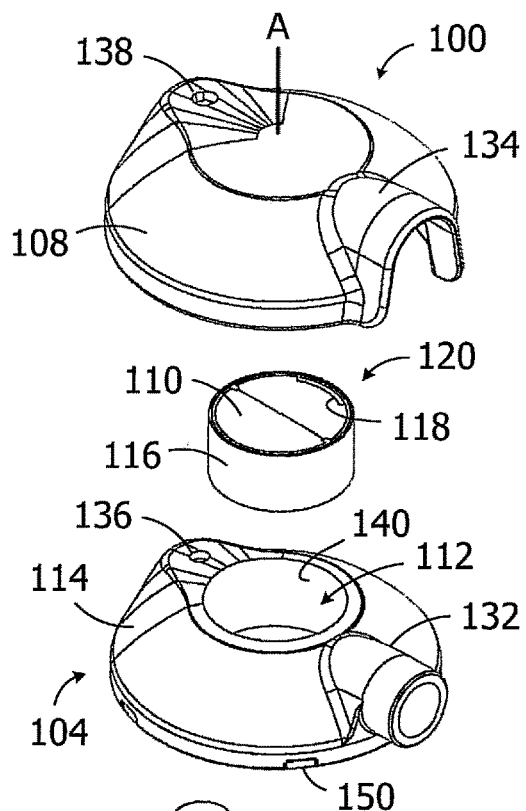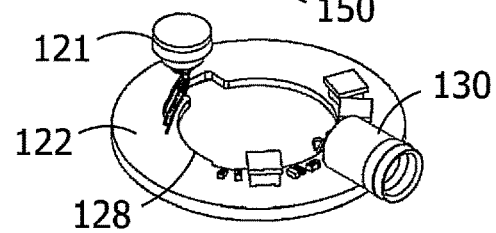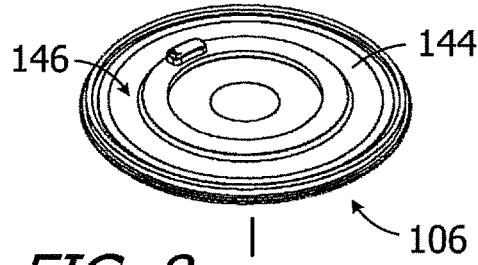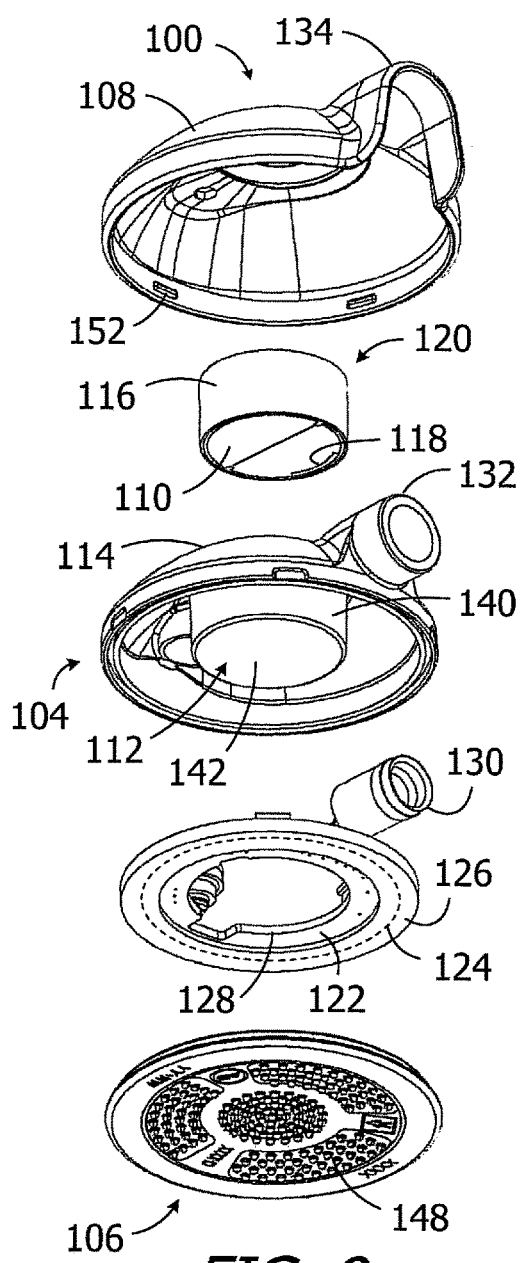

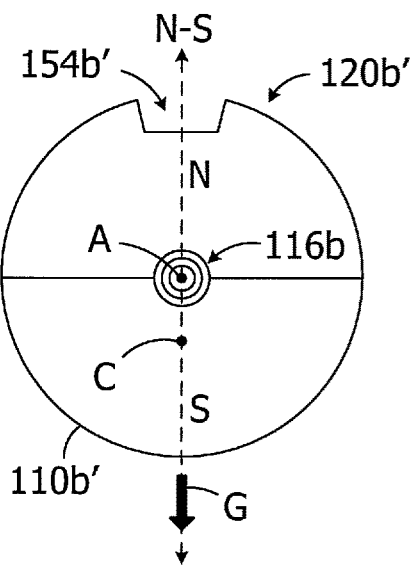
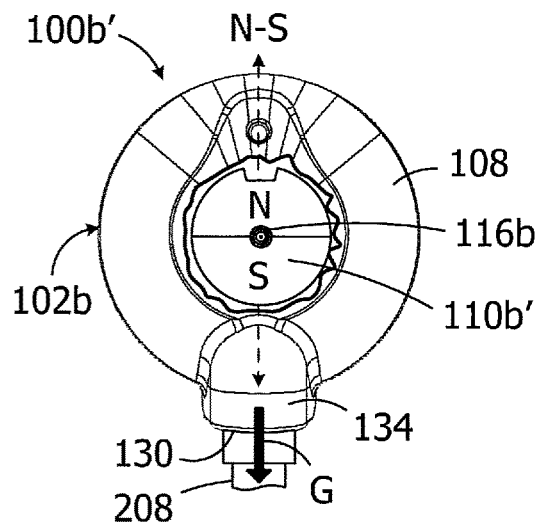
FIG. 23A    FIG. 23B
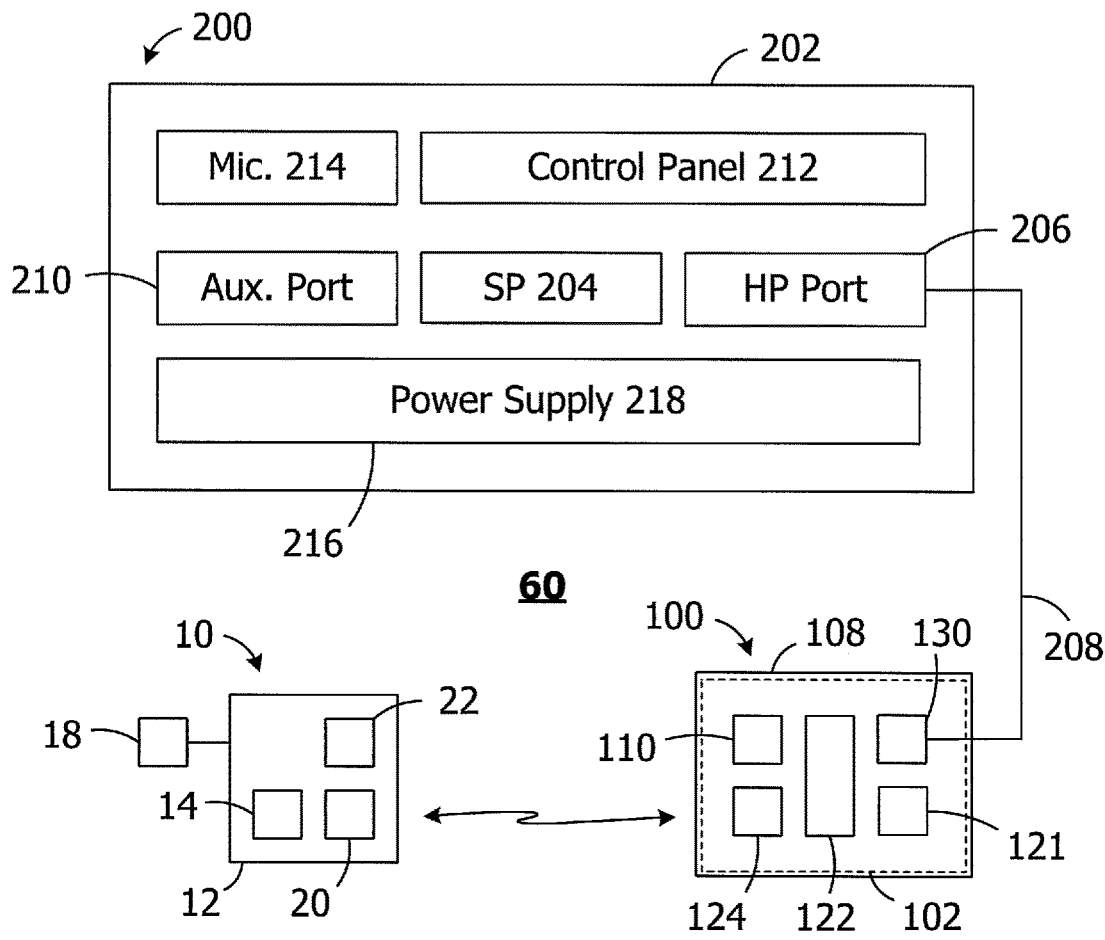
FIG. 24

HEADPIECES AND IMPLANTABLE COCHLEAR STIMULATION SYSTEMS INCLUDING THE SAME

This application is continuation of U.S. application Ser. No. 16/966,885, filed Aug. 1, 2020, now abandoned, which is the U.S. National Stage of PCT App. Ser. No. PCT/US2018/018451, filed Feb. 15, 2018.

BACKGROUND

1. Field

The present disclosure relates generally to implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit, a battery, and a microphone that is part of, or is in communication with, the sound processor unit. The cochlear implant communicates with the sound processor unit, and some ICS systems include a headpiece that is in communication with both the sound processor unit (e.g., a body worn processor or behind-the-ear processor) and the cochlear implant. The headpiece communicates with the cochlear implant by way of a transmitter (e.g., an antenna) on the headpiece and a receiver (e.g., an antenna) on the implant. The headpiece and the cochlear implant may include respective magnets (or respective pluralities of magnets) that are attracted to one another, thereby retaining the headpiece on the head and maintaining the position of the headpiece transmitter on the head over the implant receiver. The skin and subcutaneous tissue that separates the headpiece magnet and implant magnet is sometimes referred to as the "skin flap." In other instances, all of the external components (e.g., the battery, microphone, sound processor, antenna coil and magnet) are carried within a single headpiece. One example of such a system is disclosed in U.S. Pat. Pub. No. 2010/0046778, which is entitled "Integrated Cochlear Implant Headpiece," which is incorporated herein by reference in its entirety.

One issue associated with cochlear implants is compatibility with magnetic resonance imaging ("MRI") systems. For example, the magnets in many conventional cochlear implants are disk-shaped and have north and south magnetic dipoles that are aligned in the axial direction of the disk. Such magnets produce a magnetic field that is perpendicular to the patient's skin and parallel to the axial direction, and this magnetic field direction is not aligned with, and may be perpendicular to, the direction of the MRI magnetic field (typically 1.5 Tesla or more). The misalignment of the interacting magnetic fields may result in demagnetization of the implant magnet or generate a significant amount of torque on the implant magnet that can dislodge the implant magnet and induce tissue damage.

One proposed method of accommodating an MRI magnetic field involves the use of a magnet apparatus with a diametrically magnetized disk-shaped magnet that is rotatable relative to the remainder of the implant about an axis, and that has a N-S orientation which is perpendicular to the axis. One example of a cochlear implant with such a magnet is the cochlear implant 10 illustrated in FIGS. 1-3. The cochlear implant 10 includes a flexible housing 12 formed from a silicone elastomer or other suitable material, a stimulation processor 14, a cochlear lead 16 with an electrode array 18, and an antenna 20 that may be used to receive data and power by way of an external antenna. A diametrically magnetized disk-shaped magnet 22 that is rotatable about the axis A relative to the remainder of implant 10 is positioned within the antenna portion of the housing 12. The magnet 22 will rotate about the axis A into alignment with an MRI magnetic that is perpendicular to the axis A.

The cochlear implant 10 may be used in conjunction with a headpiece 30 that includes a housing 32 in which components, such as a microphone array with a pair of microphones 34 and a printed circuit board (not shown) that carries an antenna 36 and other electronic components, are located. The housing 32 includes a pair of microphone apertures 38. An electrical connector 40 connects the circuit board to a sound processor (e.g., a BTE sound processor) by way of a cable 42. A diametrically magnetized disk-shaped magnet 44 is also provided. The magnetic attraction between the magnets 22 and 44 maintains the position of the headpiece 30 against the skin flap over the cochlear implant 10, and causes the N and S poles of the rotatable implant magnet 22 to align with the S and N poles of the headpiece magnet 44 in the manner shown. U.S. Pat. No. 8,634,909 ("the '909 patent") discloses a cochlear implant system with a diametrically magnetized and rotatable disk-shaped implant magnet and a diametrically magnetized disk-shaped headpiece magnet. The '909 patent indicates that the headpiece magnet may either be fixed within the headpiece to prevent its rotation, or allowed to rotate on its axis like the implant magnet.

The microphones 34 of the microphone array are spaced along a microphone axis MA and are fixed in place, i.e., are not movable relative to the housing 32. The microphone axis MA is perpendicular to the cable 42 and, as a result, the microphone axis MA will point to the target source when, for example, the user is standing and looking at the target source.

The present inventors have determined that there are a number of issues associated with the above-described cochlear implant systems. For example, the proper retention of the headpiece 30 depends on the normal retention force NRF and the lateral retention force LRF (FIG. 3). The normal retention force NRF is a function of the strength of the diametrically magnetized implant and headpiece magnets 22 and 44 as well as the thickness of the skin flap and hair (if any), while the lateral retention force LRF is a function of the normal retention force NRF and the coefficient of friction between the headpiece and the associated head surface. Pressure on the skin flap can result in discomfort and tissue necrosis when the normal retention force NRF is too high, while the headpiece will not be retained when the normal retention force NRF is too low. Additionally, the normal retention force NRF is maximized when the N and S poles of the implant and headpiece magnets are aligned N to S and S to N and, for a given normal retention force NRF, the lateral retention force LRF is maximized when the N-S direction (or "axis") of the magnets is aligned with the gravitational direction G.

Given that headpieces are typically worn with the headpiece cable extending downwardly in the gravitational direction G (FIG. 3), some conventional headpieces fixedly align the N-S direction of the headpiece magnet with the headpiece cable, thereby typically aligning the N-S direction of the headpiece magnet with the gravitational direction G. This can be problematic for persons who do not wear their headpiece in the typical manner and instead wear the headpiece in, for example, the manner illustrated in FIG. 4. Although the strength of the headpiece magnet 44 will cause the rotatable implant magnet 22 (FIG. 3) to rotate into N-S alignment with the headpiece magnet, the N-S direction of the magnets will not be aligned with the gravitational direction G due to the fixed orientation of the headpiece magnet. Such misalignment results in a less than optimal lateral retention force LRF, and a microphone axis MA direction that may not be pointing at the target sound source when the user is looking at the target source. Similarly, in those instances where the headpiece magnet 44 is free to rotate relative to the remainder of the headpiece 30' (FIG. 5), the N-S orientation of the headpiece magnet may be misaligned with the cable 42. As such, even when the cable 42 is aligned with the gravitational direction G, the N-S direction of the magnets 22 and 44 may not be aligned with the gravitational direction G.

SUMMARY

A cochlear implant headpiece in accordance with one of the present inventions includes a housing, a diametrically magnetized headpiece magnet, defining an axis and a N-S direction, within the housing and rotatable about the axis, whereby the N-S direction of the headpiece magnet self-aligns with the gravitational direction when the axis is perpendicular to the gravitational direction, and a headpiece antenna associated with the housing. The present inventions also include cochlear stimulation systems with a sound processor and/or a cochlear implant in combination with such a headpiece. There are a variety of advantages associated with such headpieces and systems. By way of example, but not limitation, alignment of the N-S direction of the headpiece magnet with the gravitational direction maximizes the lateral retention force for a given normal retention force.

A cochlear implant headpiece in accordance with one of the present inventions includes a first headpiece portion defining a rotational axis, a second headpiece portion mounted on the first headpiece portion and rotatable relative to the first housing portion about the rotational axis, including a headpiece antenna and first and second microphones defining a microphone array axis, and having a center of gravity located such that the microphone array axis will be perpendicular to the gravitational direction when the rotational axis is perpendicular to the gravitational direction, and a headpiece magnet associated with the first headpiece portion. The present inventions also include cochlear stimulation systems with a cochlear implant in combination with such a headpiece. There are a variety of advantages associated with such headpieces and systems. By way of example, but not limitation, orienting the microphone array axis in a direction that is perpendicular to the gravitational direction, regardless of magnet orientation, increases the likelihood that the microphone array axis will point at the target sound source when the user is standing and looking at the target source.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a conventional cochlear implant.

FIG. 2 is a plan view of a conventional headpiece.

FIG. 3 is a simplified side, section view of a cochlear implant and the headpiece illustrated in FIGS. 1 and 2.

FIG. 4 is a plan view of the headpiece illustrated in FIG. 2.

FIG. 5 is a plan view of a conventional headpiece.

FIG. 6 is a perspective view of a headpiece in accordance with one embodiment of a present invention.

FIG. 7 is a perspective view of a portion of the headpiece illustrated in FIG. 6.

FIG. 8 is an exploded perspective view of the headpiece illustrated in FIG. 6.

FIG. 9 is an exploded perspective view of the headpiece illustrated in FIG. 6.

FIG. 23A is a plan view of a magnet apparatus in accordance with one embodiment of a present invention.

FIG. 23B is a cutaway plan view of a headpiece including the magnet apparatus illustrated in FIG. 23A.

FIG. 24 is a block diagram of an ICS system in accordance with one embodiment of a present invention.

DETAILED DESCRIPTION OF THE EXEMPLARY EMBODIMENTS

Figure 10:
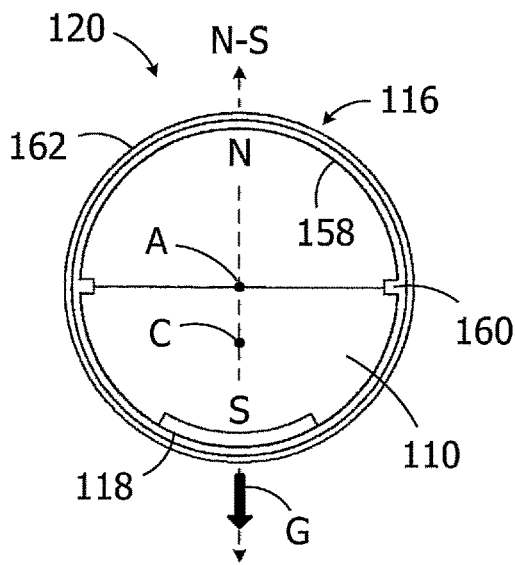
FIG. 10 is a plan view of a portion of the headpiece illustrated in FIG. 6.

The following is a detailed description of the best presently known modes of carrying out the inventions. This description is not to be taken in a limiting sense, but is made merely for the purpose of illustrating the general principles of the inventions.

An exemplary headpiece in accordance with at least one of the present inventions is illustrated in FIGS. 6-9 and is generally represented by reference numeral 100. The exemplary headpiece 100 may include a housing 102, with a main portion 104 and a cover 106, and a removable cap 108 that may be secured to the housing. A diametrically magnetized headpiece magnet (or "magnet") 110, which is rotatable about a central axis A (or "axis of rotation A"), is located within a receptacle 112 that extends to the top wall 114 of the main portion 104. The cap 108 keeps the magnet 110 within the receptacle 112. In the illustrated implementation, rotation of the magnet 110 is facilitated through the use of a glide bearing 116 that is also located within the receptacle 112 and to which the magnet 110 is secured. Other exemplary bearings that may be employed include ball bearings and needle bearings. The magnet 110 and receptacle 112 may, alternatively, be provided with extremely low friction surfaces that face one another, thereby defining an "integrated glide bearing." A weight 118 is associated with the magnet 110 in such a manner that the center of gravity of the magnet is offset from the axis of rotation A, as is described in greater detail below with reference to FIGS. 10-13. The magnet 110, glide bearing 116 and weight 118, which are also discussed in greater detail below with reference to FIGS. 10-13, form a magnet assembly 120. The magnet 110 may be removed from the magnet assembly 120 and replaced with, for example, a magnet of a greater or lesser strength.

The internal volume of the exemplary housing 102 includes a microphone 121 and a printed circuit board (PCB) 122 that is connected to the microphone and that carries various other headpiece electronic components on one side. Other implementations may include an array of two or more microphones 121. An antenna 124 is associated with housing 102, i.e., the antenna is located on, is located within, or is otherwise carried by the housing. The other side of the PCB 122 includes the antenna 124, which is within an annular protective covering 126 (FIG. 9), in the illustrated implementation. In other implementations, the antenna may be carried by the cover 106. The PCB 122 also includes an aperture 128 through which the receptacle 112 extends. A connector 130, such as a RF connector, is connected to the PCB 122 and extends through a tube 132 on the housing main portion 104. The connector 130 may be used to connect the PCB 122 to a sound processor (e.g., a BTE sound processor) by way of a cable 208 (FIG. 24). The exemplary cap 108 has a hood 134 to accommodate the connector 130 and tube 132. The housing 102 and cap 108 also include microphone ports 136 and 138 that are aligned with the microphone 121. A shield (not shown) may be positioned over the port 138 on the inner surface of the cap 108.

In the illustrated implementation, the housing main portion 104 includes a cylindrical wall 140 that define the side surface of the receptacle 112 and a bottom wall 142. The housing cover 106 includes a bottom wall 144 and an annular indentation 146 for the antenna's protective covering 126. The bottom (or "exterior") surface of the bottom wall 144 may be concave or flat, and may include a plurality of protrusions 148. The housing 102 and cap 108 may be attached to one another with any suitable instrumentalities. In the illustrated implementation, the housing main portion 104 includes a plurality of latch indentations 150 that are engaged by a corresponding plurality of latches 152 on the cap 108 when the cap is positioned over the housing 102 in the manner illustrated in FIG. 6.

Figure 11:
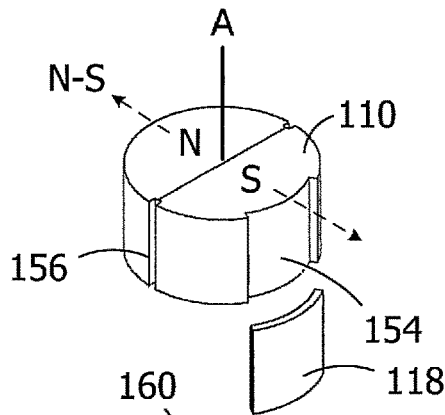
FIG. 11 is an exploded perspective view of a portion of the headpiece illustrated in FIG. 6.
Figure 12:
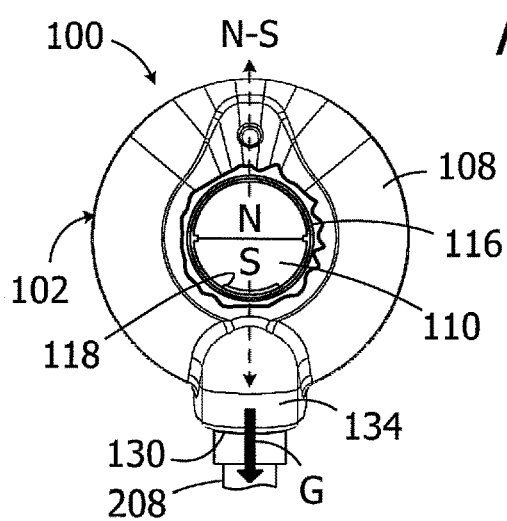
FIG. 12 is a cutaway plan view of the headpiece illustrated in FIG. 6.
Figure 13:
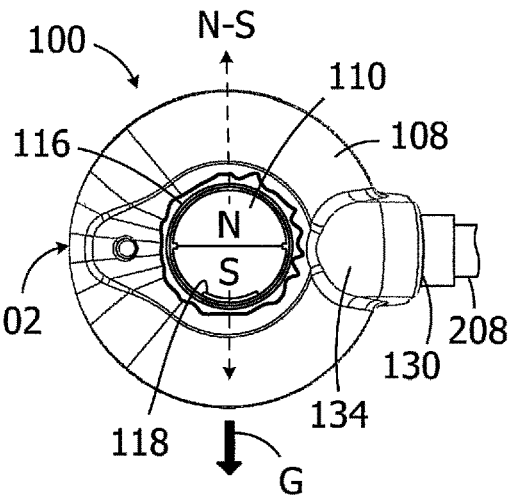
FIG. 13 is a cutaway plan view of the headpiece illustrated in FIG. 6.

The magnet, bearing and weight in embodiments of the present headpieces may be secured to, or otherwise associated with, one another in any suitable fashion. Referring to FIGS. 10 and 11, in the illustrated implementation, the exemplary diametrically magnetized magnet 110 includes an outer perimeter indentation 154 and a pair of slots 156. The exemplary glide bearing 116 includes an inner bearing member 158, with a pair of projections 160 that respectively extend inwardly into the magnet slots 156, and an outer bearing member 162. The exemplary weight 118 is configured to fit into the indentation 154 in such a manner that the magnet 110 and the weight together define a disk shape. In particular, the exemplary weight 118 is arc-shaped with a thickness corresponding to the depth of the indentation 154. The magnet 110 may be secured to the inner bearing member 158, and the weight 118 may be secured to the magnet and inner bearing member, with adhesive or any other suitable instrumentality. When the exemplary headpiece 100 is assembled in the manner illustrated in FIGS. 6 and 7, the outer surface of the inner bearing member 158 abuts and is slidable relative to the inner surface of the outer bearing member 162, and the outer surface of the outer bearing member 162 abuts and is fixed relative to the inner surface of the receptacle cylindrical wall 140. As a result, the magnet 110 and inner bearing member 158 are rotatable relative to the housing 102 about the axis A.

Referring again to FIG. 10, the exemplary weight 118 may be formed from material that has a greater density that the material that forms the magnet 110. The material may be magnetic or non-magnetic. In at least some implementations, the weight material may have a density at least 20% greater than the magnet material. For example, the magnet 110 may be formed from Neodymium, which has a density of 7 g/cm$^3$, while the weight 118 may be formed from brass or copper, which have densities of 8.6 g/cm$^3$ and 8.94 g/cm$^3$ respectively. Other suitable weight materials include tungsten and gold, which have densities of 19.3 g/cm$^3$ and 19.32 g/cm$^3$ respectively. The additional weight, as well as the location of the weight, results in the center of gravity C of the magnet/weight combination being offset from the axis of rotation A that passes through the center of the magnet 110 and being on the N-S axis of the magnet that passes through the axis of rotation A. Put another way, the magnet/weight combination results in an imbalanced load. Other methods of creating an imbalanced load are described below with reference to FIGS. 23A and 23B. When the axis of rotation A of the magnet 110 is perpendicular to the gravitational direction G, the N-S direction of the magnet will be aligned with the gravitational direction G.

There are a number of advantages associated with the exemplary headpiece. The rotatability of the remainder of the headpiece 100 relative to the magnet 110 allows the N-S direction of the magnet self-align with the gravitational direction, regardless of the preferred orientation of the headpiece 100, when the axis of rotation A is perpendicular to the gravitational direction G. In other words, if not already aligned, the magnet 110 will rotate without the application of force (other than gravitational force) in such a manner that the N-S direction of the magnet self-align with the gravitational direction, regardless of the preferred orientation of the headpiece 100, when the axis of rotation A is perpendicular to the gravitational direction G. For example, and referring to the cutaway views illustrated in FIGS. 12 and 13, the N-S direction of the magnet 110 will be aligned with the gravitational direction G when the headpiece 100 is oriented such that the cable 208 (discussed below) extends in the gravitational direction G as well as when the headpiece 100 is oriented such that the cable 208 extends in any other direction (e.g., perpendicular to the gravitational direction G). As a result, no matter how the user orients the headpiece 100, the lateral retention force LRF will be maximized for the associated normal retention force NRF.

Figure 14:
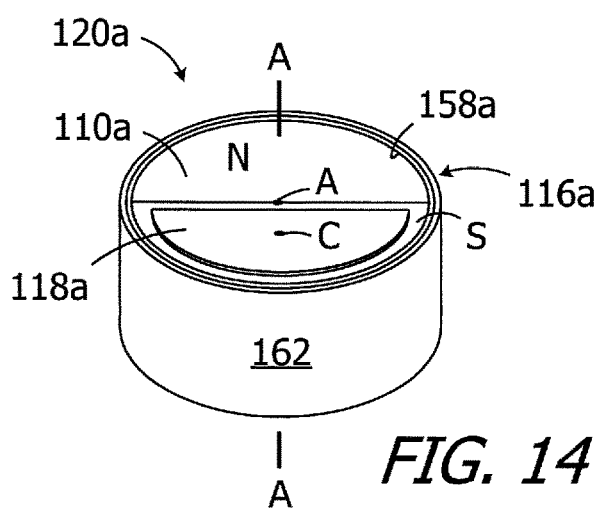
FIG. 14 is a perspective view of a magnet assembly in accordance with one embodiment of a present invention.
Figure 15:
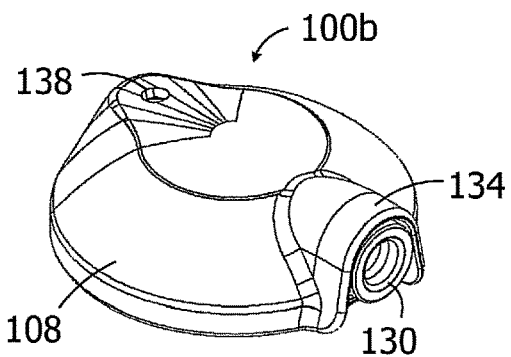
FIG. 15 is a perspective view of a headpiece in accordance with one embodiment of a present invention.
Figure 16:
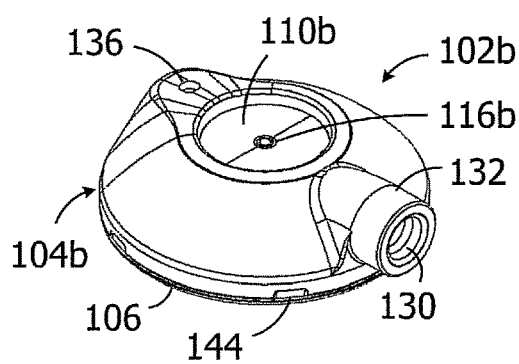
FIG. 16 is a perspective view of a portion of the headpiece illustrated in FIG. 15.
Figure 17:
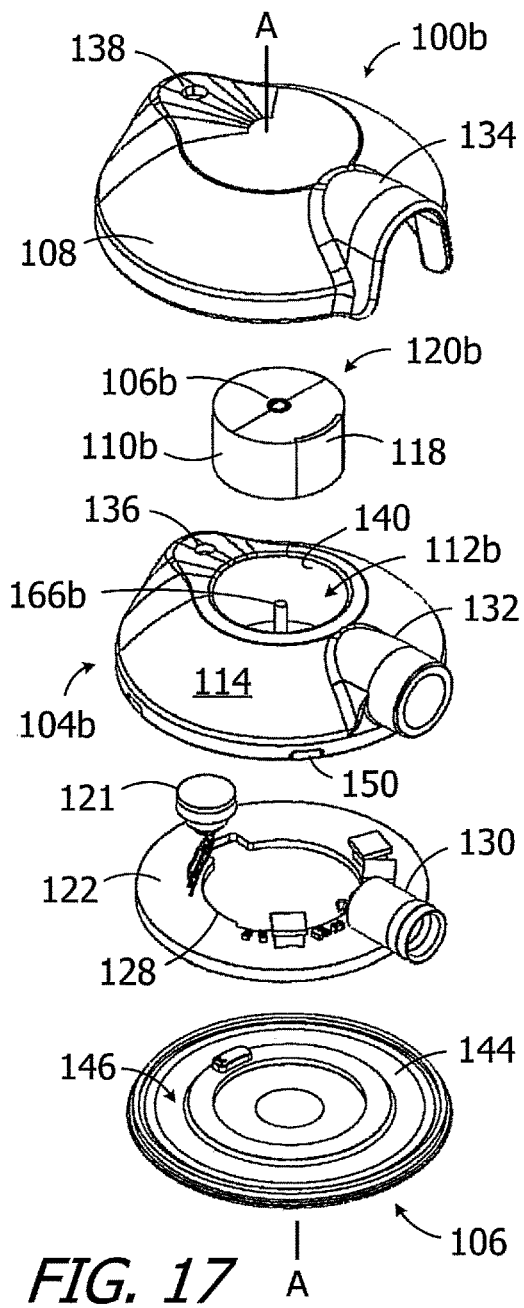
FIG. 17 is an exploded perspective view of the headpiece illustrated in FIG. 15.
Figure 18:
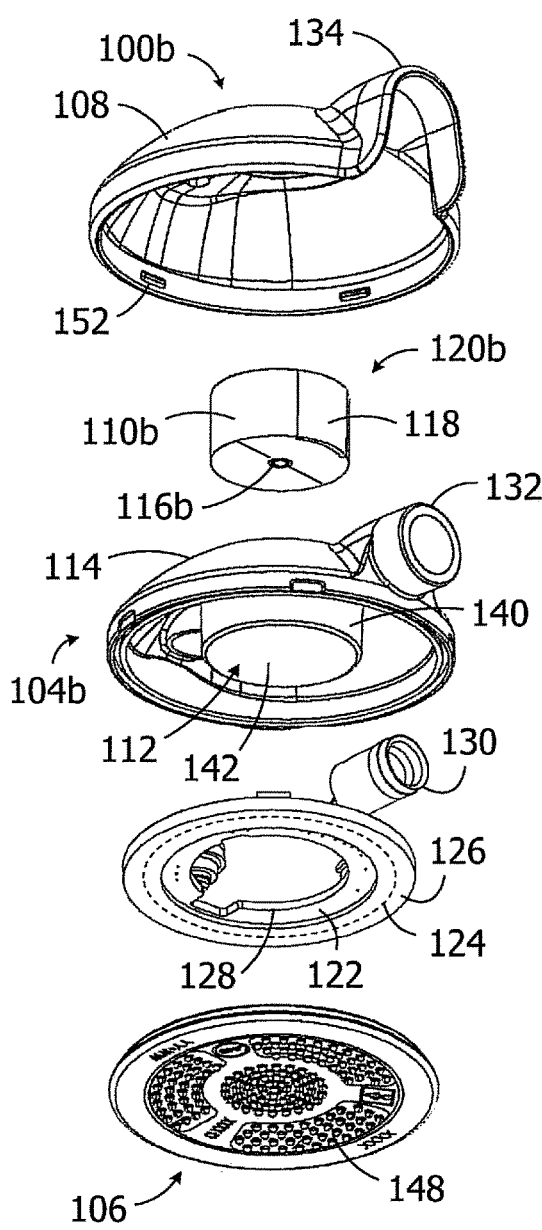
FIG. 18 is an exploded perspective view of the headpiece illustrated in FIG. 15.

It should also be noted that the present inventions are not limited to any particular bearing configuration or any particular weight shape or weight location so long as the desired rotation and off-axis center of gravity is achieved. By way of example, but not limitation, the magnet apparatus 120a in FIG. 14 is similar to magnet apparatus 120 and may be used in place of magnet apparatus 120 in the headpiece 100. For example, the magnet apparatus 120a includes a magnet 110a, a glide bearing 116a and weight 118a. The magnet 110a does not include an outer perimeter indentation for a weight, and the weight 118a is configured to be positioned on the top (or bottom) surface, i.e. the longitudinal end that faces the cap 108 (or the receptacle bottom wall 142) and extends in a directions is perpendicular to the axis of rotation A instead of parallel to axis of rotation. The top (or bottom) surface may in some instances include an indentation for the magnet. Additionally, as shown in FIG. 14, the magnet 100a does not include the above-described slots 156 (FIG. 11) and the inner bearing member 158a of the glide bearing 116a does not include the corresponding projections 160. The glide bearing 116 (or 116a) may also be omitted and the magnet 110 (or 110a) may be rotatably mounted within the housing 102 in some other way.

Figure 19:
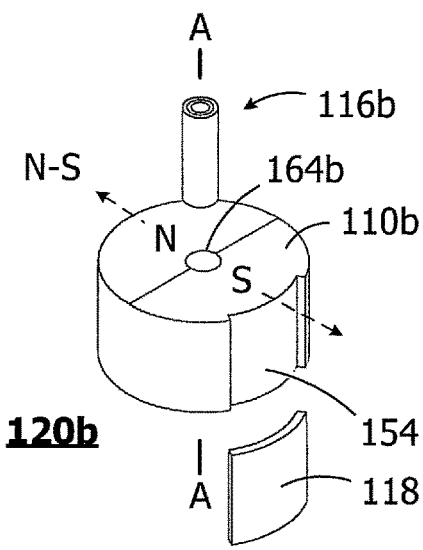
FIG. 19 is an exploded perspective view of a portion of the headpiece illustrated in FIG. 15.
Figure 20:
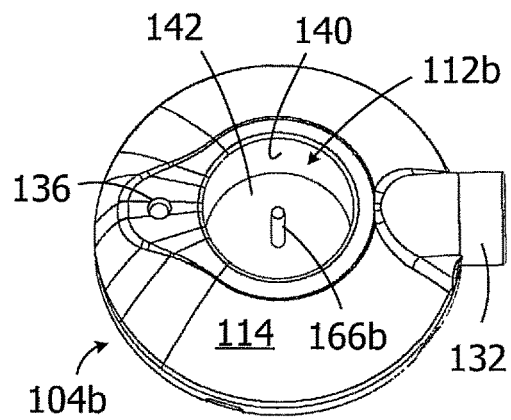
FIG. 20 is a perspective view of a portion of the headpiece illustrated in FIG. 15.

Another exemplary headpiece is generally represented by reference numeral 100b in FIGS. 15-20. The exemplary headpiece 100b is substantially similar to the exemplary headpiece 100, similar elements are represented by similar reference numerals, and the discussions above concerning like-numbered elements are incorporated here by reference. For example, the headpiece 100b may include a housing 102b, with a main portion 104b and a cover 106, and a removable cap 108 that may be secured to the housing. A diametrically magnetized headpiece magnet (or "magnet") 110b, which is rotatable about an axis of rotation A, is located within a receptacle 112b that extends to the top wall 114 of the main portion 104b. Rotation of the magnet 110b is facilitated through the use of a glide bearing 116b (with outer bearing member 158b and inner bearing member 162b) that is also located within the receptacle 112b and to which the magnet 110b is secured. Turning to FIGS. 19-20, the glide bearing 116b is located within an aperture 164b that extends through the magnet 110b and is mounted on a post 166b. The post 166b, which defined the axis of rotation A, includes a first end that is secured to the bottom wall 142 of the receptacle 112b and a second, free end. A weight 118 is associated with the magnet 110b in the manner described above. The magnet 110b, glide bearing 116b and weight 118 form a magnet assembly 120b that may be removed and replaced with, for example, an assembly that includes a magnet of greater or lesser strength.

Figure 21:
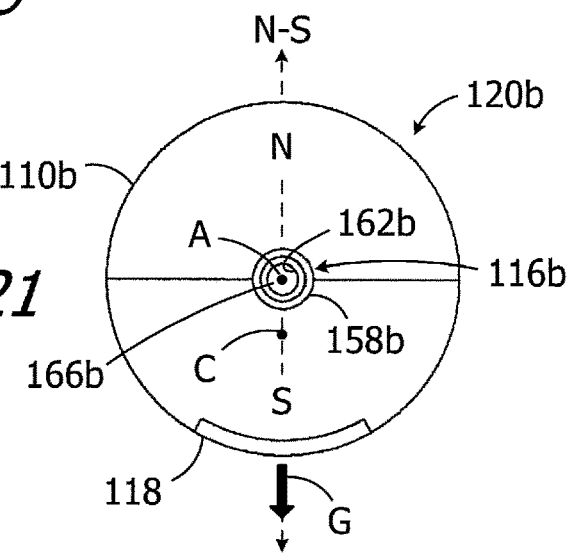
FIG. 21 is a plan view of a portion of the headpiece illustrated in FIG. 15.
Figure 22:
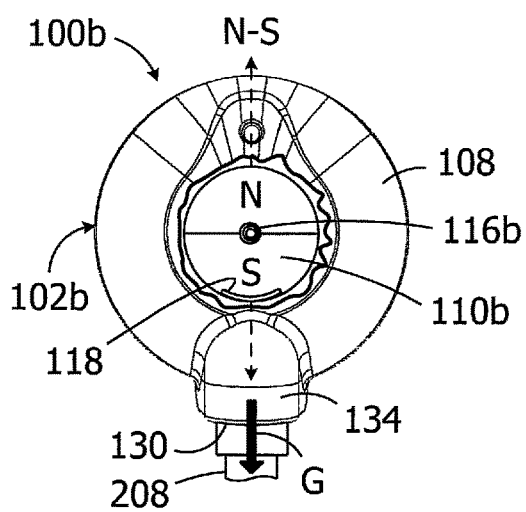
FIG. 22 is a cutaway plan view of the headpiece illustrated in FIG. 15.
Figure 23:
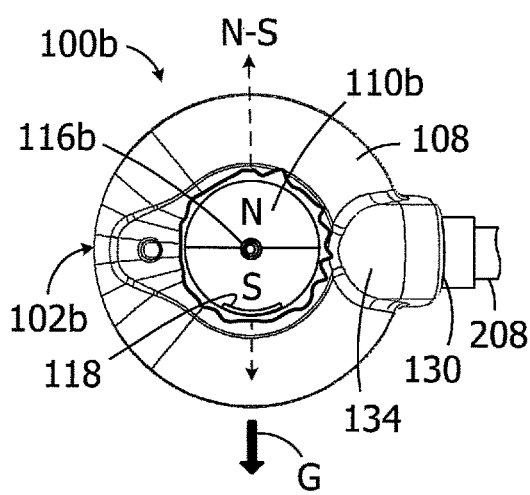
FIG. 23 is a cutaway plan view of the headpiece illustrated in FIG. 15.
Figure 25:
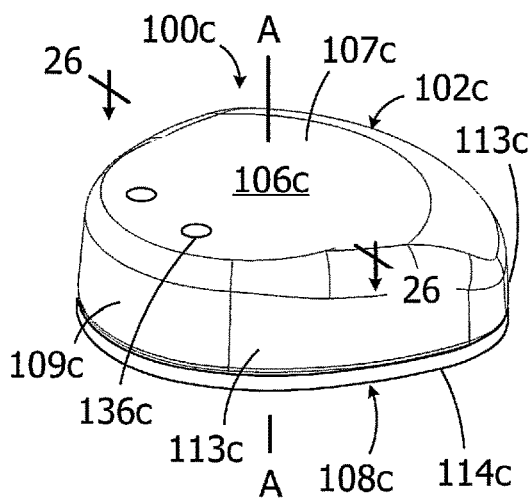
FIG. 25 is a perspective view of a headpiece in accordance with one embodiment of a present invention.

As illustrated for example in FIG. 21, and as discussed above in the context of the magnet 110, the addition of the weight 118 results in a center of gravity C that is offset from the axis of rotation A which passes through the center of the magnet 110b and being on the N-S axis of the magnet that passes through the axis of rotation A. Put another way, the magnet/weight combination results in an imbalanced load. When the axis of rotation A of the magnet 110b is perpendicular to the gravitational direction G, the N-S direction of the magnet will self-align with the gravitational direction G. Referring to FIGS. 22 and 23, relative rotational movement between the magnet 110b and the remainder of the headpiece 100, in combination with the off-axis location of the center of gravity, causes the N-S direction of the magnet to be aligned with the gravitational direction G when the axis of rotation is perpendicular to the axis A of rotation, regardless of the orientation of the headpiece 100. As such, the N-S direction of the magnet 110b will be aligned with the gravitational direction G when the headpiece 100b is oriented such that the cable 208 extends in the gravitational direction G as well as when the headpiece 100 is oriented such that the cable 208 extends in any other direction (e.g., perpendicular to the gravitational direction G).

Another exemplary magnet apparatus with an imbalanced load is generally represented by reference numeral 120b' in FIG. 23A. The exemplary magnet apparatus 120b' is substantially similar to the exemplary magnet apparatus 120b, similar elements are represented by similar reference numerals, and the discussions above concerning like-numbered elements are incorporated here by reference. For example, the magnet apparatus 120b' includes a diametrically magnetized headpiece magnet (or "magnet") 110b', which is rotatable about an axis of rotation A, as well as the aforementioned glide bearing 116b. Here, however, the magnet 110b' includes an outer perimeter indentation 154b' that does not have a weight mounted therein. The indentation 154b' functions as a region of reduced weight which, much like the region of increased weight defined by the weight 118, results in the center of gravity C being offset from the axis A. When the axis of rotation A of the magnet 110b' is perpendicular to the gravitational direction G, the N-S direction of the magnet will self-align with the gravitational direction G. Turning to FIG. 23B, the magnet apparatus 120b' may form part of a headpiece 100b' that is otherwise identical to headpiece 100b.

The exemplary headpiece 100 (or 100b or 100b') may be used in ICS systems such as, for example, the exemplary ICS system 60 illustrated in FIG. 24. The system 60 includes the cochlear implant 10, a headpiece 100 (or 100b), and a sound processor 200, such as a body worn sound processor or a behind-the-ear sound processor.

The exemplary sound processor 200 is a body worn sound processor that includes a housing 202 in which and/or on which various components are supported. Such components may include, but are not limited to, sound processor circuitry 204, a headpiece port 206 that may be connected to the headpiece 100 by a cable 208, an auxiliary device port 210 for an auxiliary device such as a mobile phone or a music player, a control panel 212, one or more microphones 214, and a power supply receptacle 216 for a removable battery or other removable power supply 218 (e.g., rechargeable and disposable batteries or other electrochemical cells). The sound processor circuitry 204 converts electrical signals from the microphone 214 into stimulation data.

During use, the above-described headpiece magnet 110 (or 110b) will be attracted to the implant magnet 22, thereby aligning the headpiece antenna 124 with the implant antenna 20. The stimulation data and, in many instances power, is supplied to the headpiece 100, which transcutaneously transmits the stimulation data, and in many instances power, to the cochlear implant 10 by way of a wireless link between the antennas. In at least some implementations, the cable 208 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 214 on the sound processor 200, the headpiece microphone 121 may be omitted in some instances.

Figure 33:
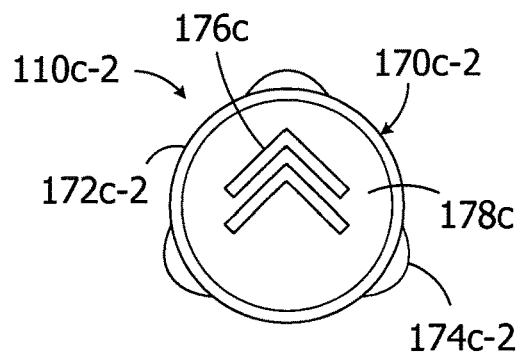
FIG. 33 is a plan view of a portion of the headpiece illustrated in FIG. 25.
Figure 34:
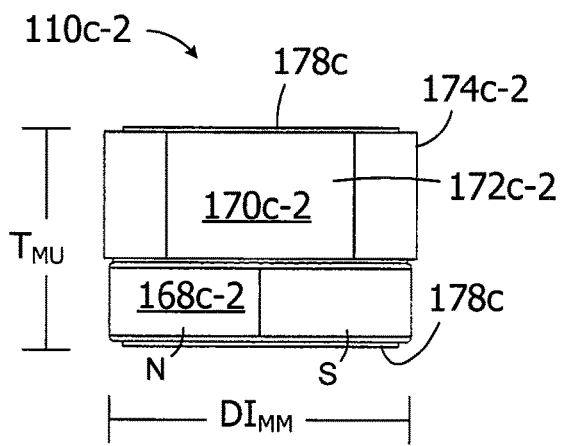
FIG. 34 is a side view of a portion of the headpiece illustrated in FIG. 25.
Figure 35:
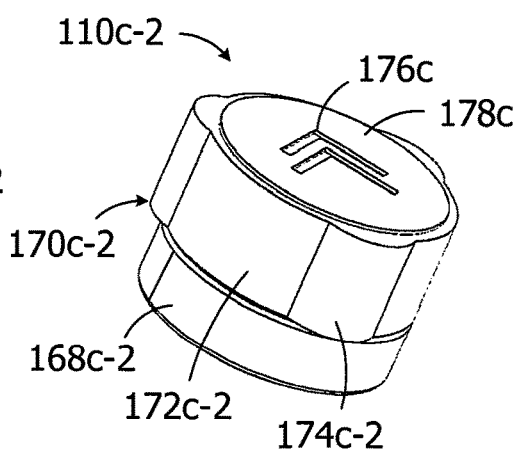
FIG. 35 is a perspective view of a portion of the headpiece illustrated in FIG. 25.

It should be noted that the present inventions have application in ICS systems which are configured such that all of the external components (e.g., the battery, the microphone, the sound processor, and the antenna coil) are carried within a single headpiece. One example of such a headpiece is generally represented by reference numeral 100c in FIGS. 25-29. The exemplary headpiece 100c may include a housing (or "headpiece portion") 102c, with a main portion 104c and a removable cover 106c, and a base (or "headpiece portion") 108c. The cover 160c has an end wall 107c, top and bottom walls 109c and 111c, and side walls 113c between the top and bottom walls. A magnet apparatus (or "magnet") 110c-2 is located within a receptacle 112c. The exemplary magnet 110c-2, which is discussed in greater detail below with reference to FIGS. 33-35, is a removable and replaceable two-part structure, including a magnetic member 168c-2 and a non-magnetic member 170c-2, which may be fixed in any desired rotational orientation relative to the receptacle 112c. The receptacle 112c is part of the base 108c, and is defined by a tubular member 115c that extends to the base bottom wall 114c, in the illustrated implementation. Once positioned within the receptacle 112c, the rotational orientation of the magnet 110c-2 relative to the receptacle 112c (and base 108c) is fixed. The housing 102c is rotatable relative to the base 108c and the magnet 110c-2 about a central axis A (or "axis of rotation A"). To that end, the main portion 104c includes a tubular member 117c in which the tubular member 115c (and receptacle 112c) is located. The tubular members 115c and 117c are both coaxial with the axis of rotation A and are connected to one another with a bearing 116c.

The internal volume of the exemplary housing 102c includes a pair of microphones 121 and a printed circuit board (PCB) 122c that is connected to the microphones and that carries the various other headpiece electronic components, such as sound processor circuitry 119, on one side. The other side of the PCB 122c includes an antenna 124. The microphones 121, which define a microphone array and are spaced along a microphone axis MA, and are fixed in place, i.e., are not movable relative to the housing 102c. Other implementations may include only one microphone 121, or more than two microphones. The PCB 122c also includes an aperture 128c through which the tubular member 117c extends. The housing has a pair of microphone ports 136c that extend through the cover end wall 107c, and shields (not shown) may be positioned over the ports 136c on the inner surface of the housing 102c. A power supply receptacle 123c for a plurality of removable power supplies 125c (e.g., rechargeable and disposable batteries or other electrochemical cells) is located within the housing 102c. Other receptacles that are configured for use with other power supplies may also be employed.

Figure 28:
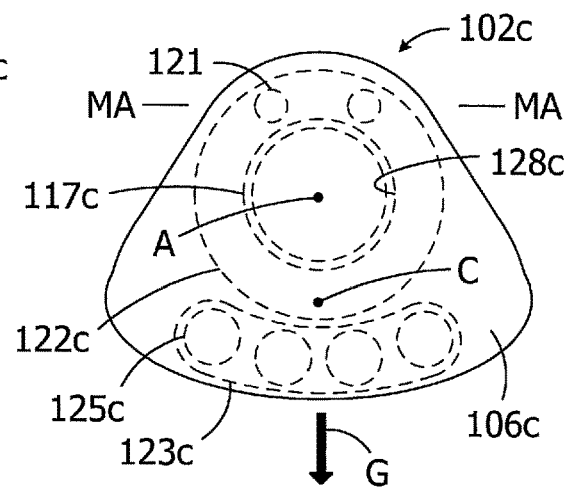
FIG. 28 is a plan view of a portion of the headpiece illustrated in FIG. 25.
Figure 29:
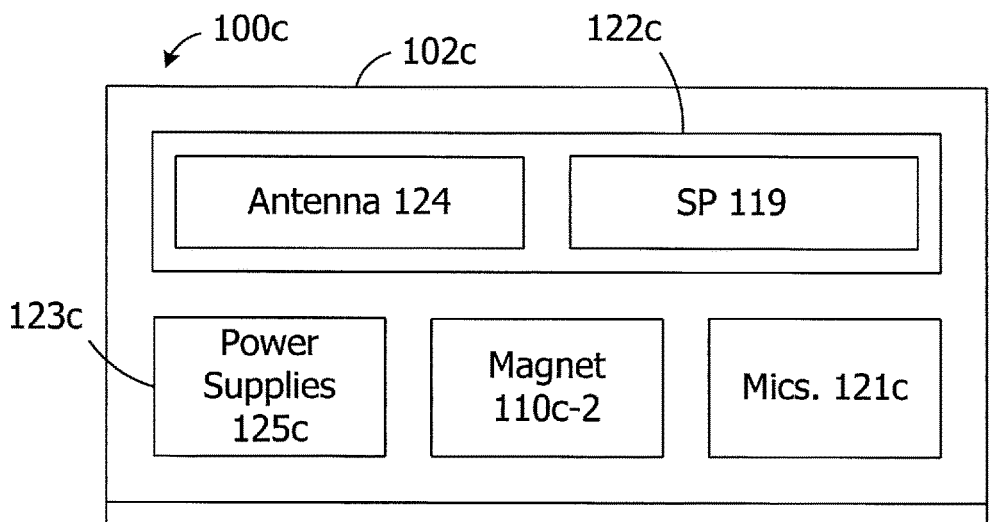
FIG. 29 is a block diagram of the headpiece illustrated in FIG. 25.
Figure 30:
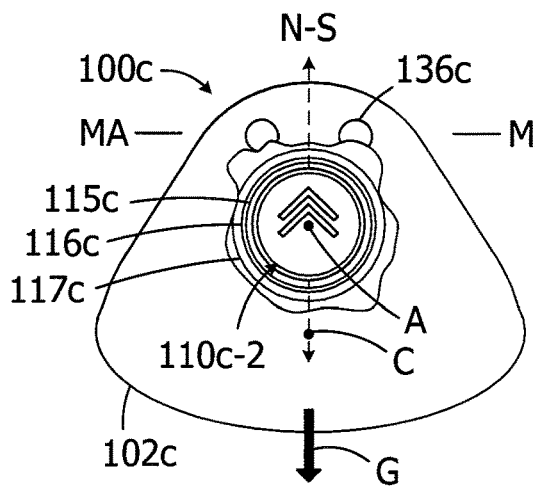
FIG. 30 is a cutaway plan view of the headpiece illustrated in FIG. 25.
Figure 31:
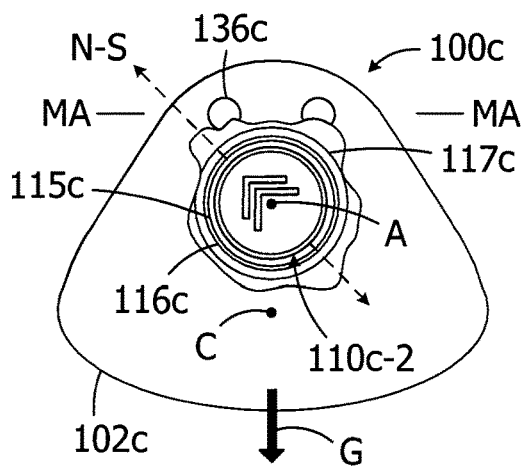
FIG. 31 is a cutaway plan view of the headpiece illustrated in FIG. 25.
Figure 32:
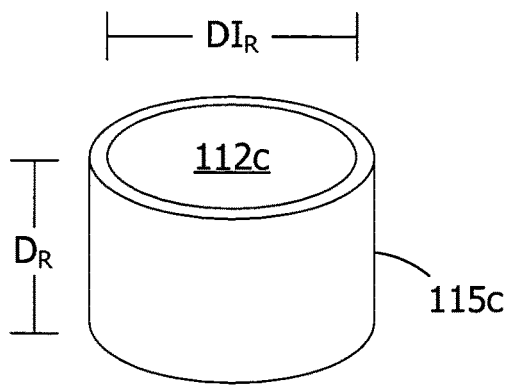
FIG. 32 is a perspective view of a portion of the headpiece illustrated in FIG. 25.

Referring more specifically to FIG. 28, the location of the relatively heavy power supplies 125c (and in some instances other relatively heavy objects) results in the center of gravity C of the housing 102c being offset from the axis of rotation A, which that passes through the respective centers of the magnet 110c-2 and the tubular members 115c and 117c. Put another way, the housing 102c has an imbalanced load. The axis A and the center of gravity C will self-align with one another in the gravitational direction G when the axis of rotation A is perpendicular to the gravitational direction G, regardless of the rotational orientation of the magnet 110c-2 and the base 108c. As a result, the microphone axis MA will point to the target source when, for example, the user is standing and looking at the target source regardless of the N-S orientation of the magnet 110c-2. To that end, and as illustrated for example in FIGS. 30 and 31, the microphone axis MA is perpendicular to the gravitational direction G when the N-S direction of the magnet 110c-2 extends in the gravitational direction G (FIG. 30) as well as when the magnet 110c-2 is oriented such that the N-S direction extends in any other direction such as, for example, 45 degrees offset from the gravitational direction G (FIG. 31).

The sound processor 119 may be operable in an omni-directional mode or in a directional mode. In the directional mode, the user points the microphone array at the target source and the sound processor 119 performs a beamforming operation on the signals from the microphones 121 in, for example, the manner discussed in U.S. Pat. No. 7,995,771, which is incorporated herein by reference in its entirety. Other directional sound processing examples are incorporated into the Phonak SmartLink+™ and ZoomLink+™ transmitters. Briefly, spatial processing is performed on the signals from the microphones 121, whereby signals associated with sound from the target sources at which (or near which) the microphone axis MA is pointing are enhanced and signals associated with sound from the non-target sources are attenuated.

The exemplary headpiece 100c may be used in ICS systems such as, for example, an exemplary ICS system that includes the cochlear implant 10.

Figure 26:
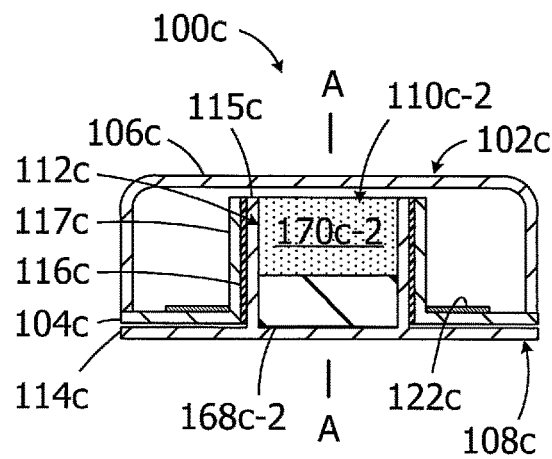
FIG. 26 is a section view taken along line 26-26 in FIG. 25.
Figure 27:
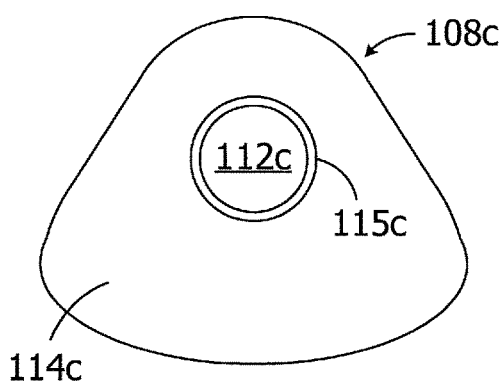
FIG. 27 is a plan view of a portion of the headpiece illustrated in FIG. 25.

Referring to FIGS. 32-35, the exemplary magnet 110c-2 is a two-part structure that includes a magnetic member 168c-2 and a non-magnetic member 170c-2 that may be permanently secured to the magnetic member. The magnetic member 168c-2 is disk-shaped, diametrically magnetized, and has a diameter $DI_{MM}$ that is identical to, or is at least substantially identical to, the diameter $DI_R$ of the receptacle 112c. The non-magnetic member 170c-2, which may be compressible and formed from foam or another compressible material, includes a disk-shaped main body 172c-2 and one or more projections 174c-2 that extend radially outward from the main body. The diameter $DI_{MB}$ of the main body 172c-2 of the compressible non-magnetic member 170c-2 is identical to, or is at least substantially identical to, the receptacle diameter $DI_R$. The uncompressed thickness $T_{MU}$ of the magnet 110c-2 is greater than the depth $D_R$. When the magnet 110c-2 is placed into the receptacle 112c (with the magnetic member 168c closest to the base bottom wall 114c), a portion of each of the projections 174c-2 will extend beyond receptacle perimeter at the top of the receptacle. The non-magnetic member 170c-2 may then be compressed into the receptacle 112c (as shown in FIG. 26) with a finger or a tool. Such compression will cause the non-magnetic member 170c-2 to press against the inner surface of the receptacle 112c, especially at the projections 174c-2, to create enough friction to maintain the magnet 112c within the receptacle and prevent the non-magnetic member from expanding back to its uncompressed state.

The exemplary magnet 110c-2 also includes indicia 176c that may be used to indicate the N-S direction of the associated diametrically magnetized magnetic member 168c-2 as well as the strength of the magnet relative to other magnets in the associated magnet system, as is described below with reference to FIGS. 36-38. In the illustrated implementation, the indicia 176c is in the form of one or more chevrons that point in the N (or S) direction. In those instances where the headpiece 100c is used in conjunction with a cochlear implant that includes a rotatable diametrically magnetized disk shaped magnet (e.g., implant 10 in FIG. 24 or one of the implants described in U.S. Pat. Pub. No. 2017/0239476, which is incorporated herein by reference in its entirety), for example, indicia 176c the user will be able to align the N-S magnetization direction of the magnetic member 168c-2 with the gravitational direction G (FIG. 30) or not align the N-S magnetization direction of the magnetic member 168c-2 with the gravitational direction G if so desired (FIG. 31).

Figure 36:
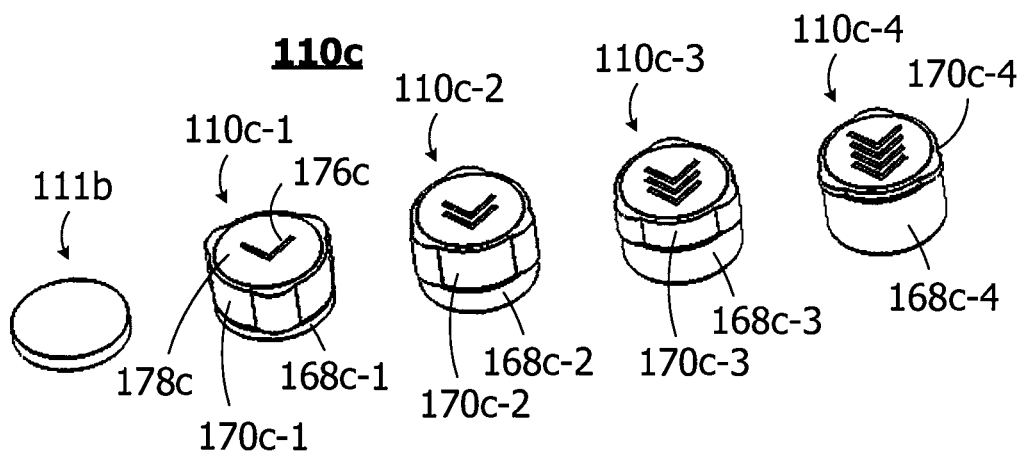
FIG. 36 is a perspective view of a magnet system in accordance with one embodiment of a present invention.
Figure 37:
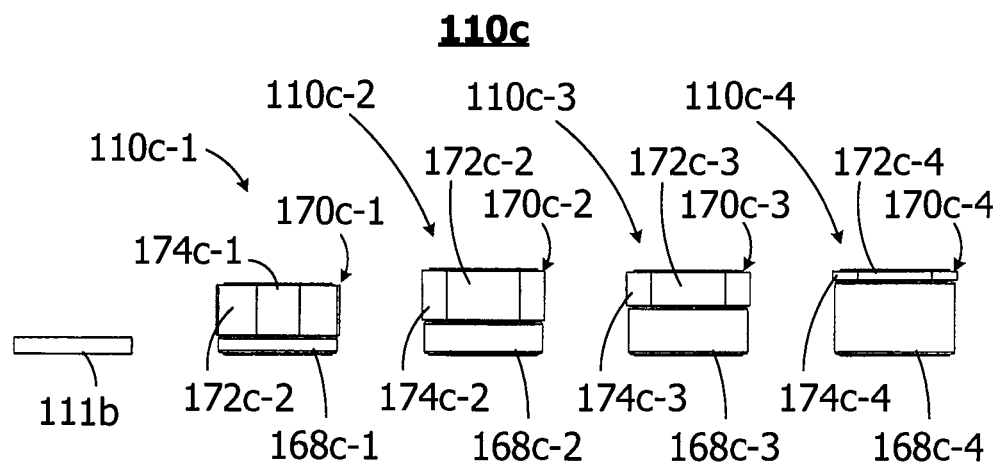
FIG. 37 is a side view of the magnet system illustrated in FIG. 36.
Figure 38:
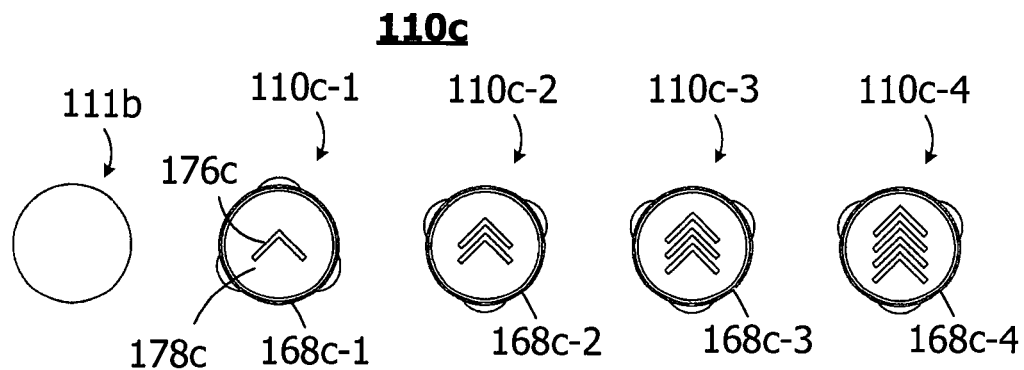
FIG. 38 is a bottom view of the magnet system illustrated in FIG. 36.

Turning to FIGS. 36-38, the exemplary magnet 110c-2 is one magnet in a multiple magnet system 110c that also includes magnets 110c-1, 110c-3 and 110c-4. The magnets in the system 110c are similar in shape and size, but have different magnetic strengths. The magnetic strength is varied from magnet to magnet by varying the sizes of the magnetic members and the compressible non-magnetic members. In particular, the magnets 110c-1 to 110c-4 are each two-part structures that each include a disk-shaped, diametrically magnetized magnetic member 168c-1 to 168c-4 and a compressible non-magnetic member 170c-1 to 170c-4 that is permanently secured to the associated magnetic member. The compressible non-magnetic members 170c-1 to 170c-4 each include a disk-shaped main body 172c-1 to 172c-4 and one or more projections 174c-1 to 174c-4 that extend radially outward from the main body. In some instances, a compressible spacer 111 (e.g., a foam spacer) may also be provided in the system 110c. The inner surface of the cap 108b may have a small recess (not shown) that can accommodate the portion of a magnet that extends beyond the receptacle 112c.

The respective uncompressed thicknesses $T_{MU}$ (FIG. 28) of the magnets 110c-1 to 110c-4 are greater than the receptacle depth $D_R$, but for the slightly shorter magnet 110c-1, while the diameters $DI_{MM}$ are the same. The respective thicknesses (and strengths) of the magnetic members increases from magnetic member 168c-1 to magnetic member 168c-4, while the uncompressed thicknesses of the non-magnetic members decreases from non-magnetic member 170c-1 to non-magnetic member 170c-4.

In the illustrated implementation, the number of chevrons 160a identifies the relative strengths of the magnets 110c-1 to 110c-4. A single chevron 176c is indicative of the weakest magnet (i.e., magnet 110c-1) and four chevrons are indicative of the strongest magnet (i.e., magnet 110c-4). Alternatively, or in addition, other types of strength representative indicia (e.g., numbers or color) may also be employed. The chevrons 160a (or other indicia) may also be provided on the top and bottom surfaces of the magnets 110c-1 to 110-4. The chevrons 176c or other indicia may, for example, be provided on adhesive labels 178c (as shown) or formed directly on the associated surfaces.

The number of magnetic strength options provided by the exemplary magnet system 110c is greater than the number of magnets in the system. The magnets 110c-1 to 110c-4, each of which has a different strength, may be inserted with the magnetic member 168c-1 to 168c-4 facing the implant magnet 22 or with the associated compressible non-magnetic member 170c-1 to 170c-4 facing the implant magnet. Put another way, the magnets 110c-1 to 110c-4 may be inserted into the receptacle 112c in such a manner that the non-magnetic member 154-1 to 154-4 is between the associated magnetic member 168c-1 to 168c-4 and the bottom wall 114c, or in such a manner that the non-magnetic member is not between the associated magnetic member and the bottom wall. The user can, therefore, select either of two possible magnetic member to implant magnet distances for each of the magnets 110c-1 to 110c-4 depending upon the insertion orientation of the magnet. Additionally, given the slightly lesser thickness of the magnet 110c-1, the compressible spacer 111b may be placed between the magnet 110c-1 and the bottom end of the reservoir 112c when the magnet 110c-1 is in either orientation. Accordingly, each of the magnets 110c-2 to 110c-4 is capable of creating two different magnetic attraction forces with the same implant magnet, while the magnet 110c-1 is capable of creating four different magnetic attraction forces with the same implant magnet.

It should also be noted that the magnet system 110c may be employed in a headpiece similar to the headpiece 100. For example, the bearing 116 may be modified in such a manner that the projections 160 are omitted and the entire bearing remains within the receptacle. Weights similar to weights 118 may be added to the magnetic members 168c in the magnet system 110c.

Figure 39:
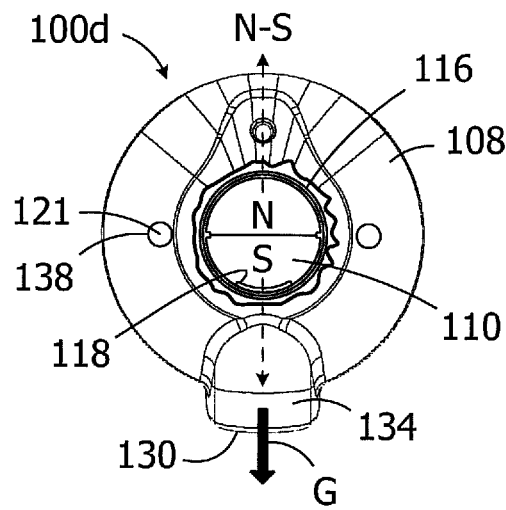
FIG. 39 is a plan view of a headpiece in accordance with one embodiment of a present invention.

The location and number of the microphones may also be adjusted as desired. By way of example, but not limitation, the exemplary headpiece 100d illustrated in FIG. 39 is essentially identical to headpiece 100 and similar elements are represented by similar reference numerals. Here, however, the headpiece 100d includes three microphones 121, which are offset from one another by 90 degrees, and the cover 108' includes three microphone ports 138 that are aligned with the microphones 121. The housing (under the cover) also has three microphone ports. Signals from the microphones 121 may be processed in a directional mode similar to that described above.

Figure 40:
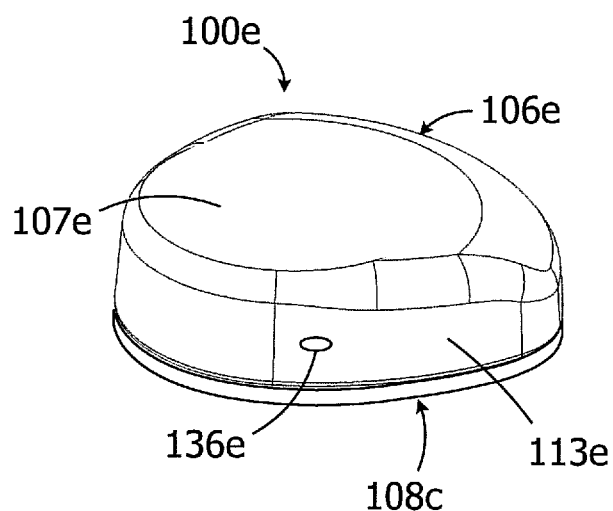
FIG. 40 is a perspective view of a headpiece in accordance with one embodiment of a present invention.

Turning to FIG. 40, the exemplary headpiece 100e is essentially identical to headpiece 100c and similar elements are represented by similar reference numerals. Here, however, the microphones face respective cover side walls 113e (instead of the end wall 107e) and the cover 106e includes microphone ports 136e (only one shown) that extend through respective cover side walls 113e. As a result, the microphones face forwardly and rearwardly. Signals from the microphones may be processed in a directional mode similar to that described above.

Figure 41:
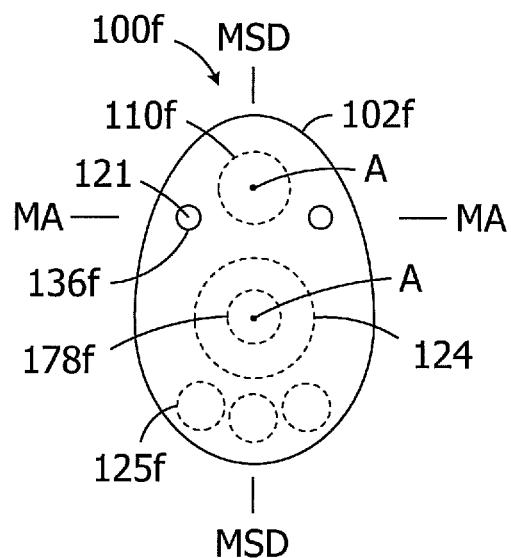
FIG. 41 is a plan view of a headpiece in accordance with one embodiment of a present invention.

Another exemplary headpiece that is configured such that all of the external components (e.g., the battery, the microphone, the sound processor, and the antenna coil) are carried within a single headpiece is generally represented by reference numeral 100f in FIG. 41. The exemplary headpiece 100f is similar to headpiece 100c in that headpiece 100f includes a housing 102f in which components such as a sound processor (not shown), a microphone array with a pair of microphones 121 (see also FIG. 25), an antenna 124, a positioning magnet 110f, and batteries 125f are located. The microphones 121 are spaced along a microphone array axis (or "microphone axis") MA and are fixed in place, i.e., are not movable relative to the housing 102f. The housing 102f includes microphone ports 136f, which may be located on an end wall (as shown) or on side walls in a manner similar to that illustrated in FIG. 40. The headpiece 100f does not include the above-described base and rotational capabilities of headpiece 100c that are used to maintain a predetermined headpiece orientation. Here, the headpiece 100f is provided with an orientation magnet 178f and is configured to be used in conjunction with a cochlear implant having a corresponding orientation magnet. Magnets 110f and 178f each define an axis A and are spaced apart from one another in a magnet spacing direction MSD such that they are not coaxial. In the illustrated implementation, the magnet spacing direction MSD is perpendicular to the microphone array axis MA.

Figure 42:
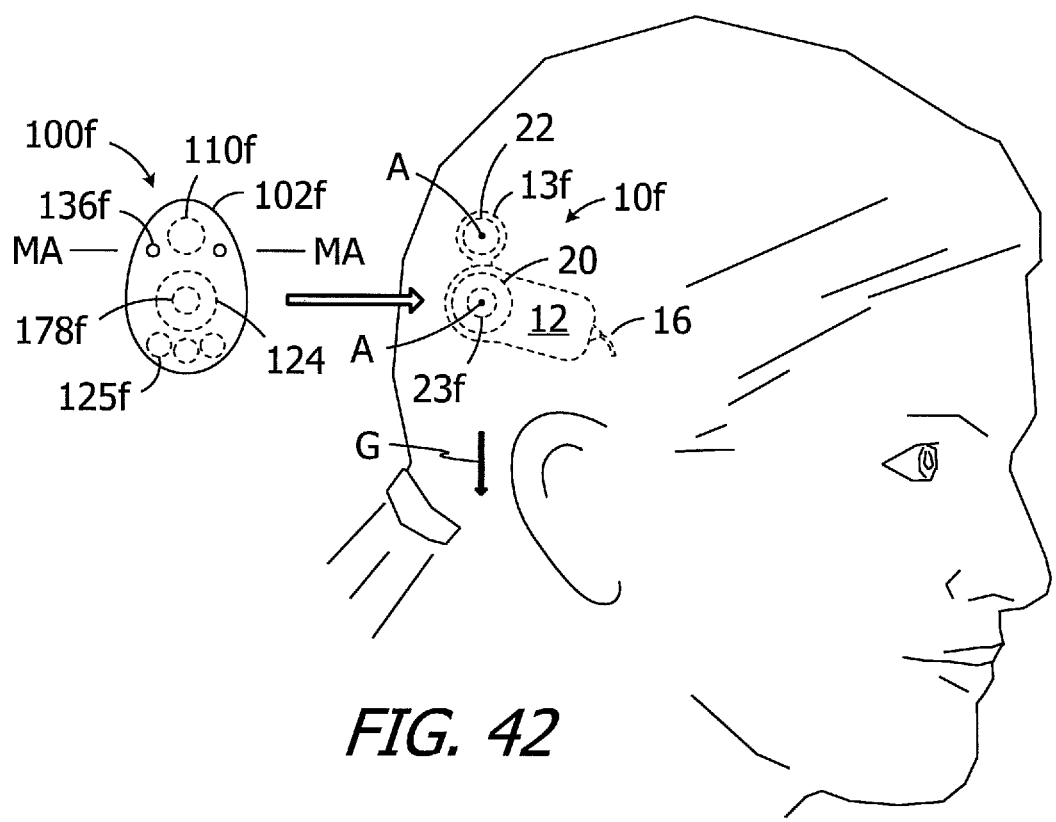
FIG. 42 is a perspective view of an ICS system including the headpiece illustrated in FIG. 41 associated with the right ear of the user.

To that end, and referring to FIG. 42, the exemplary cochlear implant 10f is substantially similar to cochlear implant 10 and similar elements are represented by similar reference numerals. Here, however, the cochlear implant 10f includes a housing 12f with a magnet carrier 13f for the magnet 22. The magnet carrier 13f may be a separate structure that is secured to the implant housing 12, or may be an integral part of the implant housing. A positioning magnet 23f is located within the antenna portion of the housing 12. Magnets 22 and 23f each define an axis A and are spaced apart from one another in such a manner that they are not coaxial.

During use, the magnets 110f and 178f of the headpiece 100f are positioned over the magnets 22 and 23f of the cochlear implant 10f. The magnets 22 and 110f retain the headpiece 100f on the user's head, while the magnets 23f and 178f align the antennas 20 and 124 and set the orientation of the headpiece 100f (and microphone array axis MA) relative to the user's head. For example, as illustrated in FIG. 42, the magnets 23f and 178f may be used to set the orientation of the headpiece 100f (and microphone array axis MA) in such a manner that the microphone array axis MA is perpendicular to the gravitational direction G when the user is standing or sitting and looking straight ahead.

The implant and headpiece magnets 22, 23f, 110f and 178f may be any suitable magnets. In some instances, such as the illustrated implementation, the implant and headpiece magnets 22, 23f, 110f and 178f may diametrically magnetized disk-shaped magnet that are rotatable relative to the remainders of the cochlear implant 10f and headpiece 100f about respective axes A in the manner described above, with or without associated bearings.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant headpiece for use with a cochlear implant, the cochlear implant headpiece comprising:
   a housing;
   a diametrically magnetized headpiece magnet, defining an axis, a N-S direction and a center of gravity that is offset from the axis, within the housing and rotatable about the axis, whereby the N-S direction of the headpiece magnet passes through the center of gravity of the headpiece magnet and self-aligns with the gravitational direction when the axis is perpendicular to the gravitational direction; and
   a headpiece antenna associated with the housing.

2. A cochlear implant headpiece as claimed in claim 1, further comprising:
   a bearing having a first bearing portion secured to the housing and a second bearing portion, rotatable relative to the first bearing portion, secured to the headpiece magnet.

3. A cochlear implant headpiece as claimed in claim 2, wherein
   the second bearing portion extends through the headpiece magnet along the axis.

4. A cochlear implant headpiece as claimed in claim 3, wherein
   the housing includes a post on the axis; and
   the first bearing portion is mounted on the post.

5. A cochlear implant headpiece as claimed in claim 1, wherein
   the headpiece magnet includes an outer perimeter indentation that does not include a weight located therein.

6. A cochlear implant headpiece as claimed in claim 1, further comprising:
   a magnet receptacle in which the headpiece magnet is located; and
   a cap configured to be mounted on the housing and to cover the magnet receptacle when mounted on the housing.

7. A cochlear stimulation system, comprising:
   a cochlear implant headpiece as claimed in claim 1; and
   a cochlear implant including a cochlear implant magnet and a cochlear implant antenna.

8. A cochlear stimulation system, comprising:
   a cochlear implant headpiece as claimed in claim 1; and
   a sound processor including
      a housing, and
      sound processor circuitry carried within the housing and operably connected to the headpiece antenna.

9. A cochlear implant system as claimed in claim 8, further comprising:
  a cochlear implant including a cochlear implant magnet and a cochlear implant antenna.

10. A cochlear implant headpiece for use with a cochlear implant, the cochlear implant headpiece comprising:
  a housing;
  a diametrically magnetized headpiece magnet, defining an axis and a N-S direction, within the housing and rotatable about the axis;
  a weight operably connected to the headpiece magnet and rotatable with the headpiece magnet; and
  a headpiece antenna associated with the housing;
  wherein
  the headpiece magnet and the weight together define a center of gravity; and
  the respective configurations of the headpiece magnet and the weight and the respective locations of the headpiece magnet and the weight relative to the axis are such that the center of gravity is offset from the axis and the N-S direction of the headpiece magnet self-aligns with the gravitational direction and passes through the center of gravity and the axis when the axis is perpendicular to the gravitational direction.

11. A cochlear implant headpiece as claimed in claim 10, wherein
  the headpiece magnet defines a disk-shape and the weight is located within the disk-shape.

12. A cochlear implant headpiece as claimed in claim 10, wherein
  the headpiece magnet includes an indentation; and
  the weight is within the indentation.

13. A cochlear implant headpiece as claimed in claim 10, wherein
  the magnet is formed from a first material having a first density; and
  the weight is formed from a second material having a second density that is greater than the first density.

14. A cochlear implant headpiece as claimed in claim 10, further comprising:
  a bearing having a first bearing portion secured to the housing and a second bearing portion, rotatable relative to the first bearing portion, secured to the headpiece magnet.

15. A cochlear implant headpiece as claimed in claim 14, wherein
  the headpiece magnet defines an outer perimeter; and
  the second bearing portion extends around the outer perimeter of the headpiece magnet.

16. A cochlear implant headpiece as claimed in claim 14, wherein
  the second bearing portion extends through the headpiece magnet along the axis.

17. A cochlear implant headpiece as claimed in claim 16, wherein
  the housing includes a post on the axis; and
  the first bearing portion is mounted on the post.

18. A cochlear stimulation system, comprising:
  a cochlear implant headpiece as claimed in claim 10; and
  a cochlear implant including a cochlear implant magnet and a cochlear implant antenna.

19. A cochlear stimulation system, comprising:
  a cochlear implant headpiece as claimed in claim 10; and
  a sound processor including
    a housing, and
    sound processor circuitry carried within the housing and operably connected to the headpiece antenna.

20. A cochlear implant system as claimed in claim 19, further comprising:
  a cochlear implant including a cochlear implant magnet and a cochlear implant antenna.

\* \* \* \* \*